United States Patent [19]

Dow et al.

[11] Patent Number: 4,841,979
[45] Date of Patent: Jun. 27, 1989

[54] ULTRASONIC PROSTATE PROBE ASSEMBLY

[75] Inventors: Julian Dow, San Clemente; Paul F. Meyers, San Juan Capistrano, both of Calif.

[73] Assignee: Capistrano Labs, Inc., San Clemente, Calif.

[21] Appl. No.: 147,793

[22] Filed: Jan. 25, 1988

[51] Int. Cl.$^4$ .............................................. A61B 10/00
[52] U.S. Cl. ................................................ 128/660.10
[58] Field of Search ................... 128/4, 6, 660, 661, 128/662, 663, 660.01, 660.09, 660.10

[56] References Cited

U.S. PATENT DOCUMENTS

| | | | |
|---|---|---|---|
| 3,955,561 | 5/1976 | Eggleton | 128/661 X |
| 4,092,867 | 6/1978 | Matzuk | 73/609 |
| 4,106,346 | 8/1978 | Matzuk | 73/614 |
| 4,246,792 | 1/1981 | Matzuk | 73/620 |
| 4,271,706 | 6/1981 | Ledly | 128/660 |
| 4,375,818 | 3/1983 | Suwaki et al. | 128/4 |
| 4,391,282 | 7/1983 | Ando et al. | 128/4 |
| 4,398,425 | 8/1983 | Matzuk | 73/633 |
| 4,399,703 | 8/1983 | Matzuk | 73/621 |
| 4,401,123 | 8/1983 | Baba | 128/6 |
| 4,421,118 | 12/1983 | Dow et al. | 73/314 X |
| 4,424,813 | 1/1984 | Havlice et al. | 128/660 |
| 4,466,443 | 8/1984 | Utsugi | 128/4 |
| 4,479,388 | 10/1984 | Matzuk | 73/634 |
| 4,483,326 | 11/1984 | Yamaka et al. | 128/4 |
| 4,545,117 | 6/1985 | Okamoto | 310/314 X |
| 4,584,880 | 4/1986 | Matzuk | 73/609 |
| 4,674,515 | 6/1987 | Andou et al. | 128/6 |
| 4,722,345 | 2/1984 | Ueno et al. | 128/660 |
| 4,756,313 | 7/1988 | Terwilliger | 128/660 |

FOREIGN PATENT DOCUMENTS 86300160.8 10/1986 European Pat. Off. ....... 128/660.10
86300150.8 12/1986 European Pat. Off. ....... 128/660.10

Primary Examiner—Francis Jaworski
Assistant Examiner—George Manuel
Attorney, Agent, or Firm—Stetina and Brunda

[57] ABSTRACT

An ultrasonic prostate probe assembly is disclosed, characterized by the ultrasonic transducer being carried upon a gimbal cup which is rotatably mounted to the probe assembly to allow selection of multiple sector scan directions during operation of the probe. The transducer is pivoted via a spring biased cable linkage connected to a linear motor having an electric coil as the reciprocating moving member. Selective rotation of the gimbal cup is effectuated by manipulation of an additional cable linkage extending axially through the probe assembly. The use of multiple sector scan directions allows improved identification and sizing of problematic body tissue in applications such as prostate applications where space constraints prevent manipulation of the probe into differing scanning positions.

12 Claims, 3 Drawing Sheets

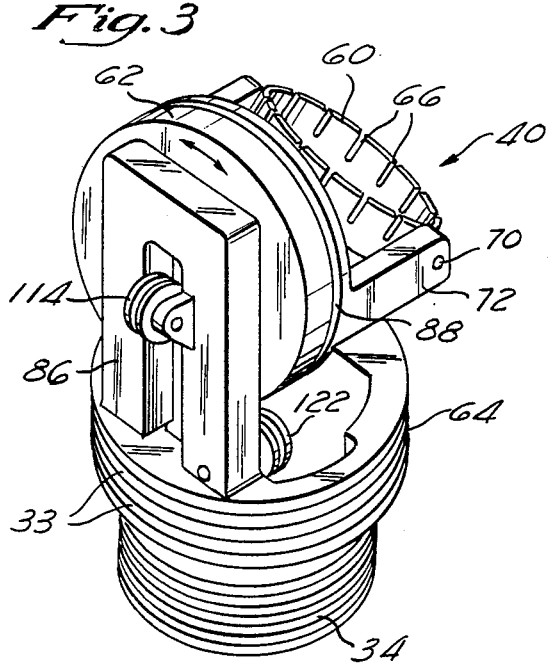
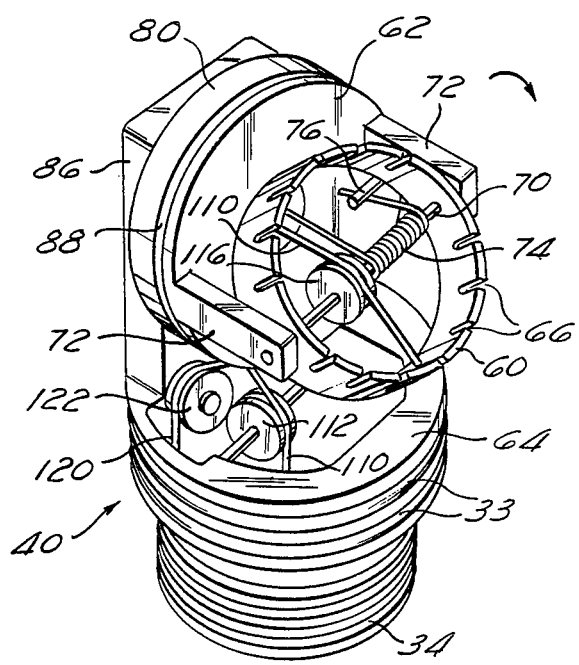
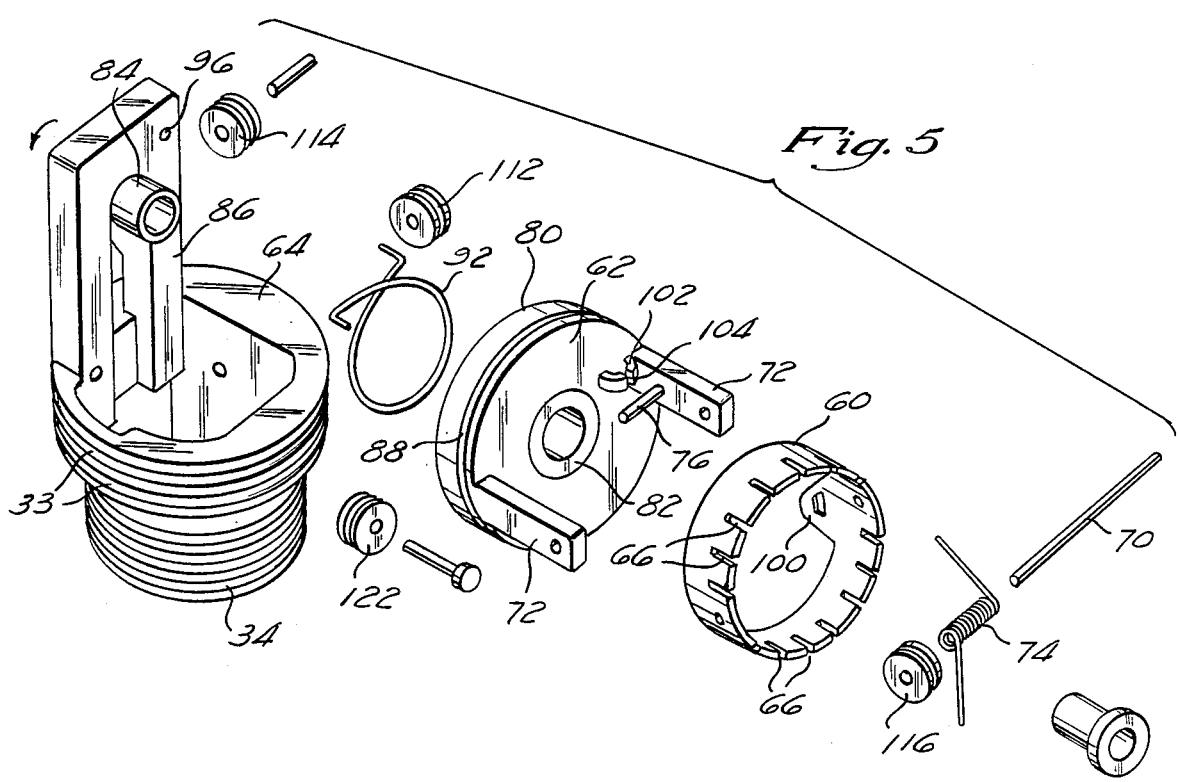

ULTRASONIC PROSTATE PROBE ASSEMBLY

FIELD OF THE INVENTION

The present invention relates to an ultrasonic transducer probe assembly for use with a real-time ultrasonic diagnostic scanner and, more particularly, to a improved ultrasonic prostate probe assembly which allows selection of multiple sector scan directions during operation of the probe assembly.

BACKGROUND OF THE INVENTION

In the field of ultrasonic diagnostics it is necessary to obtain acoustic images of body tissue. In order to produce real-time images, beams of ultrasonic energy from an ultrasonic probe are rapidly transmitted into the body tissue of a patient and echos received by the ultrasonic probe are rapidly processed in an image format suitable for display. Desirably, the probe will produce an image over a wide field of view using a sector scan format. A sector scan image is produced by repeatedly transmitting and receiving ultrasonic energy in radial directions from the probe. The ultrasonic beam is directed by a mechanically moving transducer which is physically swept about a pivot axis through an arc to produce a sector scan.

The prior art is replete with examples of ultrasonic transducer probe assemblies, such as those disclosed in U.S. Pat. No. 4,149,419 entitled "Ultrasonic Transducer Probe" issued Apr. 17, 1979 to R. Connell et al.; U.S. Pat. No. 3,955,561 entitled "Cardioscan Probe" issued May 17, 1976 to R. Eggleton; U.S. Pat. No. 4,421,118 entitled "Ultrasonic Transducer" issued Dec. 20, 1983 to J. Dow et al.; U.S. Pat. No. 4,479,388 entitled "Ultrasonic Transducer and Drive System" issued on Oct. 30, 1984 to T. Matzuk; U.S. Pat. No. 4,399,703 entitled "Ultrasonic Transducer and Integral Drive Circuit Therefor" issued on Aug. 23, 1983 to T. Matzuk; U.S. Pat. No. 4,092,867 entitled "Ultrasonic Scanning Apparatus" issued on June 6, 1978 to T. Matzuk; U.S. Pat. No. 4,246,792 entitled "Self-Contained Ultrasonic Scanner" issued Jan. 27, 1981 to T. Matzuk; and U.S. Pat. No. 4,398,425 entitled "Ultrasonic Scanning Transducer" issued on Aug. 16, 1983 to T. Matzuk. In addition, an ultrasonic transducer probe assembly is disclosed in the subject co-applicant's copending U.S. patent application Ser. No. 047,479 filed on May 11, 1987 entitled "Ultrasonic Transducer Probe Assembly".

Although all of the above-referenced patent disclosures address varying problems associated with the use of ultrasonic transducer imaging, none have addressed the particular problems associated with the use of ultrasonic transducer probe assemblies in applications such as prostate applications, where space constraints prevent manipulation of the probe to effectuate differing scan directions to allow proper identification and sizing of problematic or diseased body tissue in a patient. As such, the use of ultrasonic imaging technique in the detection of body disorders or disease associated in space intensive applications has been limited and has not fully reached its full potential as a preferred diagnostic tool. Thus, there exists a substantial need in the art for an ultrasonic imaging probe assembly which permits multiple scan directions without the requirement of manual repositioning of the probe into differing scan positions which are prohibitive due to space constraints in the intended application of use.

SUMMARY OF THE PRESENT INVENTION

The present invention specifically addresses and alleviates the above-referenced deficiencies associated in the art by providing an ultrasonic transducer probe assembly for use with a real-time ultrasound diagnostic scanner and, more particularly, by providing an improved ultrasonic probe assembly specifically adapted for use in space constraining applications such as encountered in prostate diagnostc applications.

The ultrasonic prostate probe assembly of the present invention is characterized by use of a novel construction wherein the ultrasonic transducer is carried upon a gimbal cup which is rotatably mounted to the probe assembly to allow selection of multiple scan directions during operation of the probe. The transducer is pivoted via a spring biased flexible cable linkage which is connected to a linear motor having an electric coil as a reciprocating moving member. Selective rotation of the gimbal cup is effectuated by manipulation of an additional cable linkage extending axially through the probe assembly which disposes the pivot axis for the transducer at differing orthogonal positions. As such, when the probe is inserted into its application environment, ultrasonic imaging can be effectuated in a first sector scan direction and subsequently without repositioning the probe within its application environment, the transducer pivot access may be rapidly reoriented from its first position wherein a second ultrasonic imaging procedure can be effectuated in a second sector scan direction. By viewing the multiple scan direction images displayed, a medical practitioner can better identify and size discovered problematic body tissue in the environment for diagnostic purposes.

In addition, the present invention comprises an ultrasonic prostate probe assembly which is extremely small in size so as to be suitable for use in prostate applications and may be easily manipulated by a medical practitioner. The probe includes a latex or elastomeric bladder which is positioned over the distal end of the probe to cover the transducer dome, which bladder is adapted to be selectively filled and expanded by a liquid infused through the interior of the probe. The expansion of the bladder radially outward from the transducer dome insures that air is expelled from the application environment and that a liquid environment suitable for transmission of ultrasonic waves between the probe transducer and the patient is maintained. The liquid infusion line is provided with a valve adjacent the opposite end of the probe which permits adjustment of the amount of fluid infused or vented from the bladder.

The selective rotation of the gimbal cup to allow multiple scanning direction is effectuated by the manipulation of a turn wheel or adjustment knob located at the distal end of the probe, which adjustment knob may be calibrated if desired to allow an indication of the precise positioning of the transducer pivot axis and scan direction of the transducer.

DESCRIPTION OF THE DRAWINGS

These as well as other features of the present invention will become more apparent upon reference to the drawings wherein:

FIG. 3 is an enlarged perspective view of the gimbal cup transducer mounting arrangement utilized in the present invention;

FIG. 4 is an enlarged perspective view of the gimbal cup mounting arrangement depicting the manner in which the transducer ring is pivotally mounted thereon;

FIG. 5 is an exploded perspective view of the gimbal cup mounting arrangement of the present invention;

DETAILED DESCRIPTION OF THE PREFERRED EMBODIMENT

Figures 1, 2:
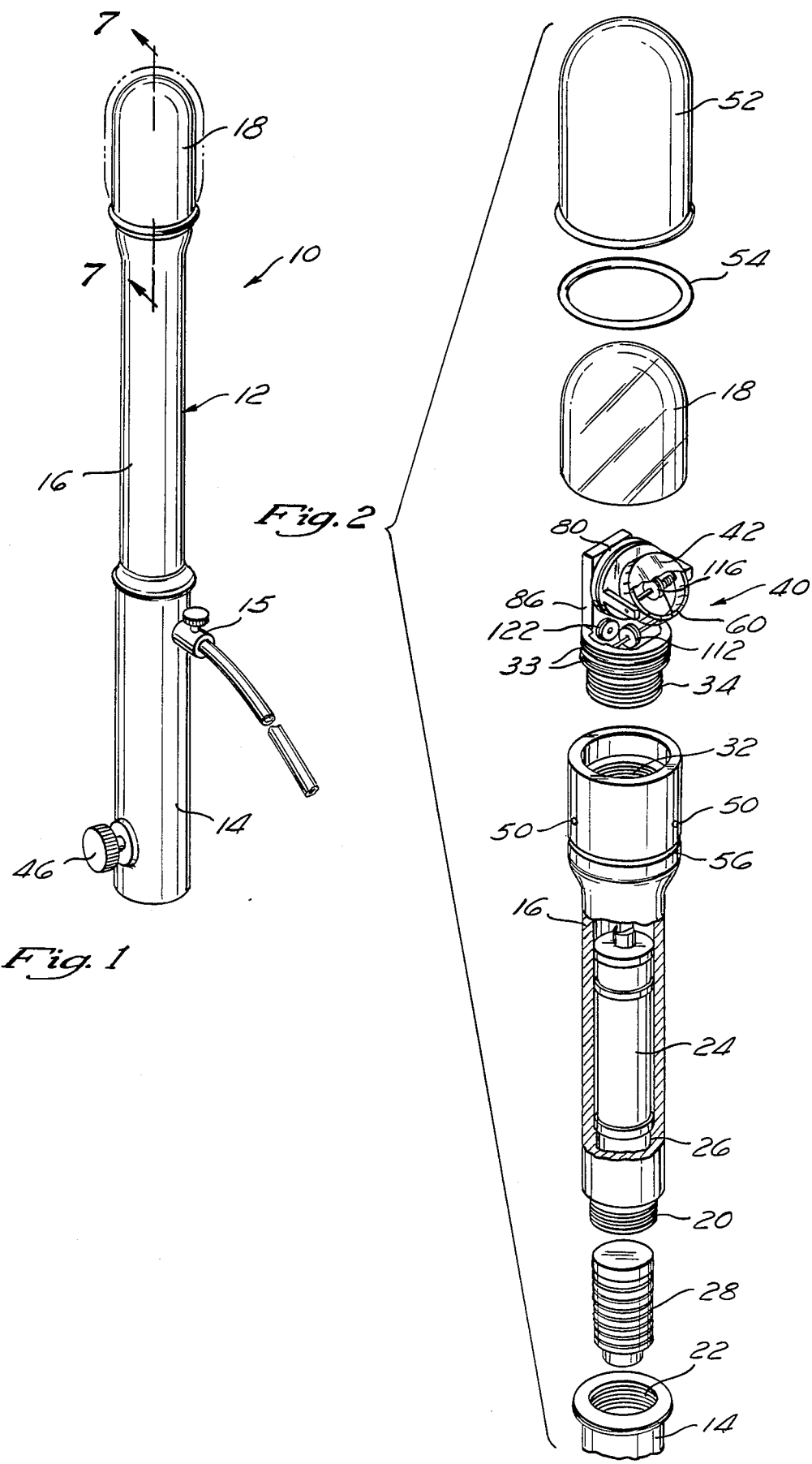
FIG. 1 is a perspective view of the ultrasonic prostate probe assembly of the present invention.
FIG. 2 is an exploded perspective view of the ultrasonic prostate probe assembly of the present invention showing its major components.

Referring to the Figures, the present invention comprises an ultrasonic transducer probe assembly designated generally by the numeral 10, which by way of example and not limitation, is specifically adapted to space contraining applications such as those encountered in prostate diagnostic applications. Referring more particularly to FIG. 1, the probe 10 is formed having a generally cylindrical housing 12 defining a handle portion 14, motor housing portion 16 and transducer dome portion 18, which are preferably arranged in a coaxial orientation. The housing 12 is relatively compact in size as required for use in prostate diagnostic applications having an approximate diameter of one inch and axial length of approximately 14 inches. The handle portion 14 and motor housing portion 12 may be machined from aluminum or stainless steel or may be molded of a suitable polymer such as delrin teflon or other suitable material. The transducer dome portion 18 is preferably formed of polyethylene or other polymer material which is highly transmissive to ultrasound waves. The distal end of the handle portion 14 includes a coaxial central aperture (not shown) through which cabled connection is made via a cable (not shown) to suitable power supplies, signal generators, and signal processors which are employed as is conventional in the use of probes for ultrasonic imaging.

As best shown in FIG. 2, the probe motor housing portion 16 and handle portion 14 are interconnected via complementary threaded sections 20 and 22 respectively, and both include a central aperture extending axially throughout their length. A linear motor 24 is disposed within the interior of the central aperture formed in the motor housing portion 16 and seats against a shoulder 26 formed on the inside diameter of the central aperture. A bladder 28 containing a sealed quantity of a compressible gas such as air is preferably located beneath the linear motor 24 within the handle portion 14. The bladder is preferably formed having a rippled or bellowed external configuration which allows the bladder 28 to moderately expand or contract axially in response to pressure exerted thereupon. As such, as temperatures existing within the interior of the probe increase during use of the probe, the bladder 28 compensates for such thermal expansion and contraction which could otherwise cause leakage within the probe.

The linear motor 24 includes a portion of its axial coil extending upwardly through its top surface, which in operation reciprocates axially back and forth above the upper surface of the motor. In the preferred embodiment the linear motor 24 is constructed in conformity with the principals and disclosure contained in coapplicant's copending U.S. patent application Ser. No. 047,479 filed May 11, 1987 entitled "Improved Ultrasonic Transducer, the disclosure of which is expressly incorporated herein by reference. However, other types of linear motors may be utilized without departing from the spirit of the present invention.

The upper end of the motor housing portion 16 is enlarged and includes a threaded bore 32 which mates with complementary formed threaded shand portion 34 formed on the lower end of the gimbal cup transducer assembly 40. One or more O-ring seals 33 may additionally be provided on the upper enlarged diameter of the shank portion 34 to provide a fluidic seal between the interface of the transducer assembly 40 and motor housing portion 16. As will be explained in more detail infra, the gimbal cup transducer assembly 40 pivotally mounts a transducer 42 which is driven back and forth about its pivot or scanning axis by the coil 30 via a linkage. The gimbal cup transducer assembly 40 additionally allows for the pivot axis of the transducer 42 to be selectively rotated in a clockwise and counter-clockwise direction as viewed in FIG. 2 via a cable linkage extending to a thumb wheel knob 46 disposed at the lower distal end of the handle portion 14.

The transducer dome 18 is sealingly connected to the upper end of the motor housing portion 16 and serves to encapsulate the gimbal cup transducer assembly 40 within the interior of the probe 10. The entire interior of the probe 10 is preferably filled with a non-toxic fluid, such as oil, which acts as both a lubricant to the mechanical components of the probe 10 as well as an ultrasound couplant. One or more fluid flow channels (not shown) extend axially from the upper end of the motor housing portion 16 to a valve 15 formed on the handle portion 14. The flow conduits terminate in one or more apertures 50 extending radially through the exterior of the motor housing portion 16. An expandable bladder 52 preferably formed of latex or an elastomeric material is positionable over the upper end of the probe to cover the transducer dome portion 18 and upper portion of the motor housing portion 16. The bladder 52 is retained upon the probe 10 by way of an O-ring 54 which may be seated within a peripheral groove 56 formed in the motor housing portion 16. The O-ring 54 forms a fluid tight seal about the lower end of the exapandable bladder 52. The valve 15 may be connected to a suitable fluid supply system wherein a fluid such as water, may be selectively introduced under pressure through the valve 15, flow channels and apertures 50 to expand the bladder 52 with fluid. As will be recognized, when in an operative environment, the expansion of the bladder 52 with fluid from a fluid source will insure that a liquid medium condusive for the transmission of ultrasound exists between the transducer 42 and the body tissue of the patient. When it is desired to remove the probe from its application environment, the fluid supply system attached to the valve 15 may be utilized to vent or apply a moderate vacuum to the valve 15 wherein fluid previously introduced into the bladder 52 may be removed therefrom.

Referring more particularly to FIGS. 3, 4 and 5, the detailed construction of the dimbal cup transducer assembly 40 may be described. The assembly 40 is basically comprised of an ultrasonic transducer 42 (shown only in FIG. 2) transducer ring or cup 60, gimbal cup mounting member 62 and a support member 64. The transducer 42 is preferably seated in the transducer ring 60 by a slight compression snapping action which is facilitated by a slight expansion of the transducer ring 60 permitted by axial slots 60 formed about its periphery. This permits incorporating during manufacture a variety of transducers of different characteristics, each of which is retained in a transducer ring 60 of the same outside dimension. The transducer ring 60 is mounted for pivotal movement about an axle 70. (i.e. scanning axis) which is journaled between a pair of support arms or struts 72 extending outwardly from the gimbal cup mounting member 62. A biasing member or spring 74 is positioned upon the axle 70, opposite ends of which contact or are fixed to a pin stop 76 formed on one of the support struts 72 and the lower periphery of the transducer ring 60. The biasing spring 74 is designed to continuously bias the transducer ring 60 in a clockwise pivoting direction as indicated by the arrow in FIG. 4. As such, the transducer ring 60, as well as the transducer 42 mounted thereon is gimbaled for back and forth pivotal movement about the axle 70 as depicted by the phantom and full line positions of FIG. 7 and is constantly biased toward the phantom line position shown in FIG. 7 by the biasing spring 74.

Figure 6:
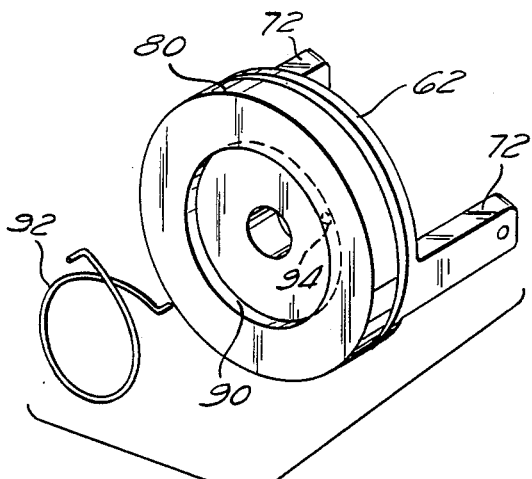
FIG. 6 is an enlarged perspective view of the gimbal cup of the present invention.
Figure 7:
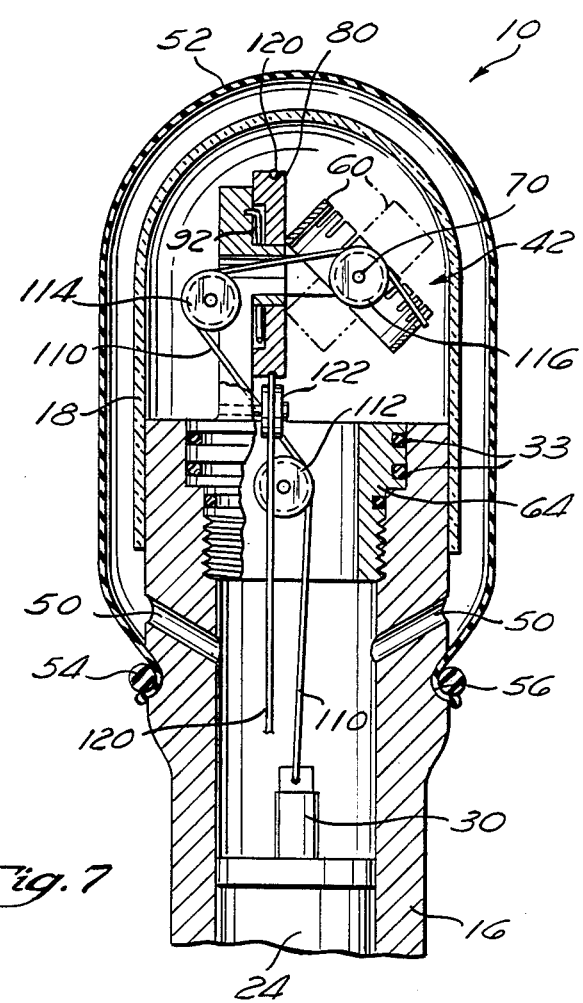
FIG. 7 is enlarged cross-sectional view taken about lines 7—7 of the FIG. 1.

The gimbal cup mounting member 62 is formed having a substantially cylindrical base member 80 having a central bearing 82 adapted to be rotatably received upon a bushing 84 formed upon a U-shaped strut 86 of the support member 64. The outer periphery of the base member of the gimbal cup mounting member 62 is provided with a peripheral groove 88, while the rear surface of the base member 80 is formed to have a cylindrical recess 90 (as best illustrated in FIG. 6). A coil spring biasing member 92 is disposed within the recess 90, one end of which is received within an aperture 94 formed within the recess 90 and the opposite end of which is received in an aperture 96 formed within the U-shaped support strut 86. As such, when the gimbal cup mounting member 62 is mounted upon the support member 64 as depicted in FIGS. 3, 4 and 7, the biasing spring 92 constantly urges or biases the gimbal cup mounting member to rotate in a counter-clockwise direction about the bushing 84 as indicated by the arrow in FIG. 5.

As illustrated in FIG. 5, the transducer ring 60 is provided with an axially extending flange 100 which cooperates with a toroidal coil 102 affixed as an insert upon the base portion 80 of the gimbal cup mounting member 62. The gap 104 of the toroidal coil 102 is variably entered by the flange 100 of the transducer ring 60, dependent upon the pivot position of the transducer ring 60 about the axle 70. The lower edge of the flange 100 is formed as a contour so that a variable amount of the flange 100 formed of a ferrous metal material will be rotated, i.e. passed within the gap 104, of the toroidal coil 102 in an amount corresponding to the varying tilt angle of the transducer ring 60 and transducer 42. As such, during pivotal movement of the transducer ring 60, the change in the amount of the flange 100 moving through the coil 102 will change the inductance of the coil 102 in a manner which may be sensed by interconnected electronic circuitry of the system (not shown). Accordingly, the toroidal coil 102, which is variably entered within its gap 104 by the flange 100, constitutes a sensor of the angular tilt, i.e. pivotal position of the transducer 42.

The transducer ring 60 is pivoted back and forth about its axle 70 by the reciprocating driving force imparted by the coil 30 of the linear motor 24. A flexible cable linkage 110 is connected to the coil 30 and extends axially upward through the central aperture formed in the support member 64 and through the interior bushing 84 and terminates at a rigid connection made along the periphery of the transducer ring 60. As best illustrated in FIG. 7, the extension of the flexible cable linkage 110 is guided by plural pulleys 112, 114 and 116 with pulley 112 being mounted within the interior of the central aperture in the support member 64, pulley 114 being mounted upon the rear surface of the U-shaped strut 86 of the support member 64 and pulley 116 being rigidly mounted upon the axle 70 of the transducer ring 160. As will be recognized, during reciprocal movement of the coil 30 of the linear motor 24, the flexible cable linkage 110 will impart a corresponding pivotal movement of the transducer ring 60 and transducer 40 mounted thereon between the full line and phantom line position shown in FIG. 7. Further, it will be recognized that during the pivotal movement from the phantom line to full line position, shown in FIG. 7, the reciprocating motion of the coil 30 will overcome the moderate biasing force of the biasing spring 74 cooperating with the transducer ring 60.

As previously mentioned, the gimbal cup mounting member 62 is journaled for rotational movement about the axis of the bushing 84. In the preferred embodiment, selective rotational movement of the gimbal cup mounting member 62 is additionally accomplished by a cable linkage 120 which is illustrated in FIG. 7. As shown, the cable linkage 120 extends axially within the interior of the probe 10 and extends over a pulley 122 rotatably mounted to the lower end of the U-shaped support strut 86. After extending over the pulley 122, the cable linkage 120 extends about a portion of the circumference of the gimbal cup mounting member 62 (as illustrated in FIGS. 4 and 7) and is rigidly mounted to the periphery of the base portion 80 of the gimbal cup mounting member 62 adjacent the side opposite to that shown in FIGS. 4 and 7. The cable linkage 120 is disposed within the peripheral groove 88 as it extends about the periphery of the gimbal cup mounting member 62. The opposite end of the flexible cable linkage 120 extends axially through the interior of the linear motor housing portion 16 and handle portion 14 of the probe and is affixed by conventional means to the axis of the turn wheel or knob 46. As such, by rotational movement of the turn wheel 46, the cable linkage 120 imparts a selective rotational movement to the gimbal cup mounting member 62 about the central axis of the bushing 84. During this selective rotational movement it will be recognized that the cable 120 overcomes the slight biasing force of the biasing spring 92, causing the effective diameter of the spring 92 to be reduced or compressed. In the preferred embodiment the gimbal cup mounting member 62 is adapted to be rotated through at least a ninety degree arc, whereby the orientation of the pivot axle 70 of the transducer ring 60 and transducer 42 is moved from its generally horizontal position shown in FIGS. 3 and 4 to a vertical position (not shown). Subsequently, when it is desired to return the gimbal cup mounting member 62 to a different rotational position, rotation of the thumb wheel 46 in an opposite direction will allow the biasing spring 92 to return the same to its original position (illustrated in FIGS. 3 and 4).

The with structure defined, the operation of the ultrasonic prostate probe assembly 10 of the present invention can be described. Initially, the probe 10 is inserted into its diagnostic application environment within the patient and when properly positioned, the valve 15 may be throttled to cause fluid to be inserted between the bladder 52 and the transducer dome 18 via apertures 50. When a sufficient amount of fluid has been introduced into the bladder 52 to cause an expansion of the same to insure a liquid interface between the transducer 42 and the body tissue of the patient, operation of the linear motor 24 causes a back and forth pivotal movement of the transducer 42 about the axle 70 wherein imaging in a first scanning direction is accomplished by the probe 10. Subsequently, without repositioning of the probe 10, the turn wheel 46 may be manipulated, causing the gimbal cup mounting member 62 to be rotated about the bushing 84 into a different rotational orientation. Operation of the linear motor 24 will then allow imaging of the patient in a second scanning direction. As such, by use of differing multiple scanning directions, a medical practitioner can obtain better ultrasonic imaging to allow more precise identification and sizing of problematic body tissue within the patient.

Those skilled in the art will recognize that various modifications can be made to the present invention without departing from the spirit of the the same and such modifications are clearly contemplated herein. In addition, no reference has been made to the various electrical interconnections made between the electronic components of the probe, such as the linear motor 24 and toroidal coil sensor. The details of such interconnections and operation of the same in an overall ultrasonic imaging system is well known in the art. However, the details of such electrical interconnections are thoroughly disclosed in co-applicant's previously mentioned copending U.S. patent application Ser. No. 047,479 filed on May 11, 1987 entitled "Improved Ultrasonic Transducer", the disclosure of which has previously been and is hereby restated to be incorporated herein by reference.

What is claimed is:

1. An ultrasonic probe assembly comprising:
   a housing;
   ultrasonic transducer means pivotally disposed within said housing for generating and receiving ultrasonic waves; means coupled to said ultrasonic transducer means for defining a scanning axis therefore
   motor means for generating a reciprocating motion for pivoting said transducer means about said scanning axis;
   means for biasing said transducer means in a first pivotal direction about said scanning axis;
   a flexible linkage extending between said motor means and said transducer means for translating reciprocal motion of said motor means to pivotal motion of said transducer means about said scanning axis; and
   means for selectively rotating said means for defining a scanning axis to enable pivoting of said transducer means in multiple scanning directions within said housing.

2. The ultrasonic probe assembly of claim 1 wherein said transducer means is mounted upon a support member rotatably mounted within said housing.

3. The ultrasonic probe assembly of claim 2 further comprising a linkage mounted to said support membeer to rotate said support member into multiple rotational orientations.

4. The ultrasonic probe assembly of claim 3 wherein said linkage comprises a cable extending within said housing.

5. The ultrasonic probe assembly of claim 4 further comprising at least one pulley means mounted within said housing for guiding said cable within said housing.

6. The ultrasonic probe assembly of claim 4 wherein said selective rotating means comprises a turn wheel mounted to said housing and connected to said cable.

7. The ultrasonic probe assembly of claim 6 wherein said flexible linkage comprises a cable.

8. The ultrasonic probe assembly of claim 7 further comprising:
   an expansible bladder mounted within a portion of said housing adjacent said transducer; and
   flow channel means formed in said housing for supplying fluid to said expansible bladder.

9. The ultrasonic probe assembly of claim 8 further comprising a valve disposed upon said housing for controlling the introduction and exit of fluid in said flow channel means.

10. The ultrasonic probe assembly of claim 2 further comprising means mounted on said support member for biasing said support member in a first rotational direction.

11. The ultrasonic probe assembly of claim 10 wherein said support member biasing means comprises a spring.

12. The ultrasonic probe assembly of claim 1 wherein said transducer biasing means comprises a spring.

* * * * *